United States Patent [19]
Forman

[11] Patent Number: 5,826,588
[45] Date of Patent: Oct. 27, 1998

[54] LASER ABLATION OF ANGIOPLASTY CATHETERS AND BALLOONS

[75] Inventor: Michael R. Forman, St. Paul, Minn.

[73] Assignee: Schneider (USA) Inc., Minneapolis, Minn.

[21] Appl. No.: 956,963

[22] Filed: Oct. 23, 1997

Related U.S. Application Data

[62] Division of Ser. No. 582,371, Jan. 11, 1996, Pat. No. 5,733,301.

[51] Int. Cl.$^6$ .......................... A61B 19/00; A61M 29/00

[52] U.S. Cl. .......................... 128/898; 606/192; 604/96; 600/207

[58] Field of Search .......................... 604/96–104; 606/1, 606/190–200; 600/201, 207; 128/898

[56] References Cited

U.S. PATENT DOCUMENTS

| Re. 33,561 | 3/1991 | Levy . |
| 3,733,309 | 5/1973 | Wyeth et al. . |
| 4,456,000 | 6/1984 | Schjeldahl et al. . |
| 4,490,421 | 12/1984 | Levy . |
| 4,906,244 | 3/1990 | Pinchuk et al. . |
| 4,941,877 | 7/1990 | Montano, Jr. . |
| 4,963,313 | 10/1990 | Noddin et al. . |
| 5,267,959 | 12/1993 | Forman . |
| 5,525,388 | 6/1996 | Wand et al. . |
| 5,733,301 | 3/1998 | Forman .................................. 606/192 |

OTHER PUBLICATIONS

"Self–developing photoetching of poly(ethylene terephthalate) films by far–ultraviolet excimer laser tradition" by R. Srinivasan, et al, Appl.Phys.Lett. 41(6), Sep. 15, 1982, pp. 576–578.

"Ultraviolet Laser Ablation of Organic Polymer Films", by R. Srinivasan, et al (1984).

"X–ray photoelectron spectroscopy studies on polymer surfaces after KrF ablation" by Kokai, et al, SPIE vol. 1190 Laser/Optical Processing of Electronic Materials (1989), pp. 95–103.

"Excimer Laser Micromachining and Surface Microstructure Modification of Polymer Films", by P.E. Dyer, et al, Nov. 1–Nov. 3.

Primary Examiner—Glenn K. Dawson
Attorney, Agent, or Firm—Haugen and Nikolai, P.A.

[57] ABSTRACT

A dilatation balloon (20,98) is fabricated according to a process that yields high hoop strength and uniformity in balloon wall thickness. A length of tubing (34) is axially elongated and radially expanded in a form (36) to provide the requisite biaxial orientation and strength. Then, an excimer laser (46,66,84) is used to remove the polymeric material by photo-chemical ablation, virtually without thermal effects. Dilatation balloon walls are thinned primarily along tapered sections (26,28) between proximal and distal balloon stems (30,32) and a medial working section (24) of the balloon. Material removal, particularly near the balloon stems, enables tighter wrapping of the balloon for a reduced delivery profile, and reduces rigidity near the stems for better maneuverability of the catheter in tortuous passageways. The balloon tapered sections are reduced to a wall thickness substantially equal to that of the medial section. Alternatively, an array of grooves (96) is formed in each tapered section.

23 Claims, 4 Drawing Sheets

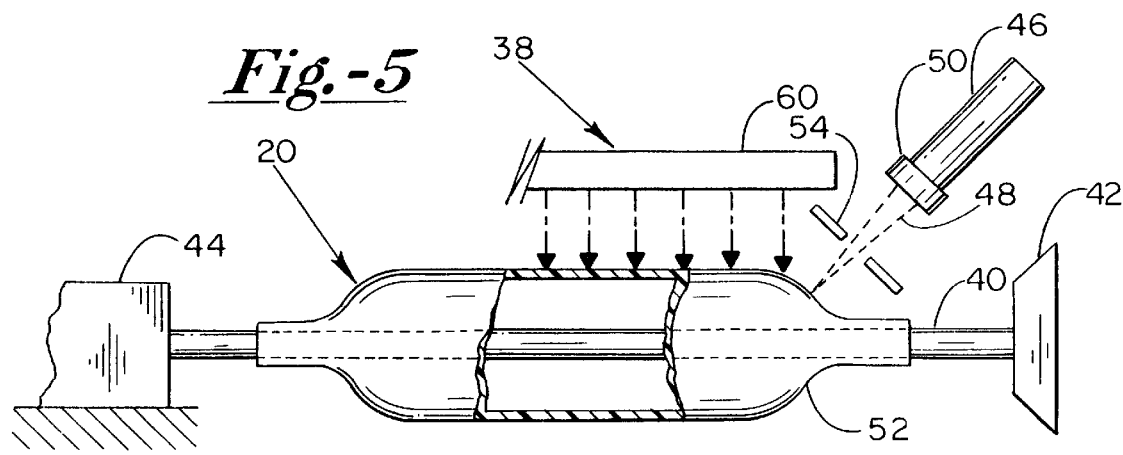
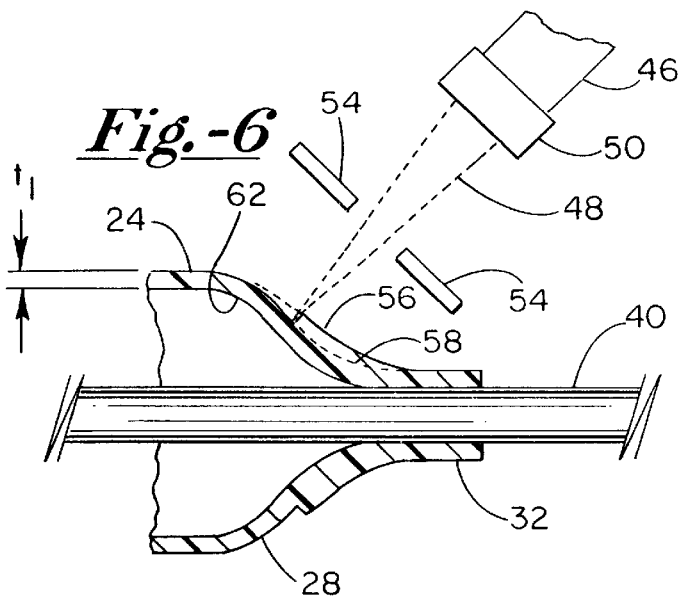
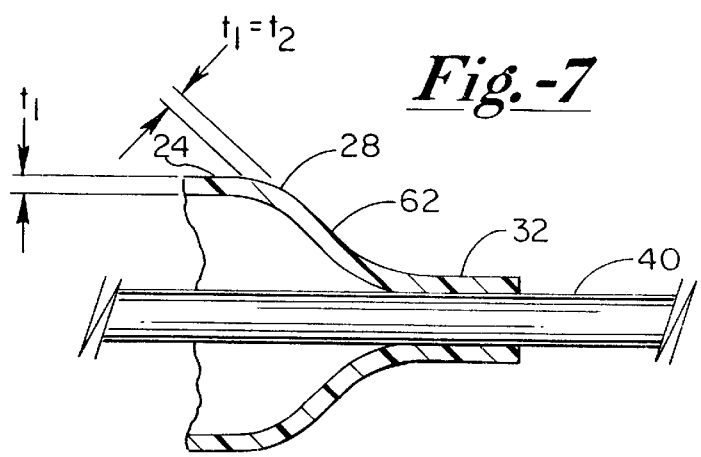

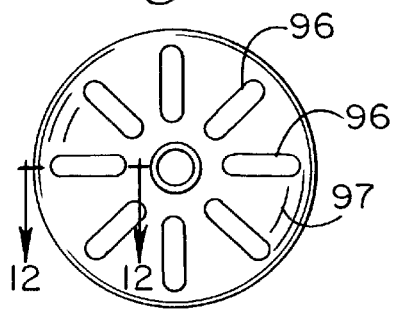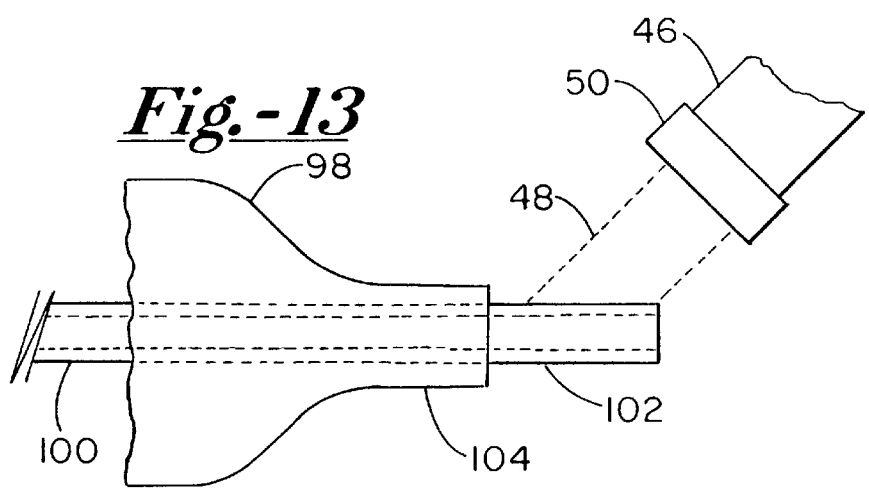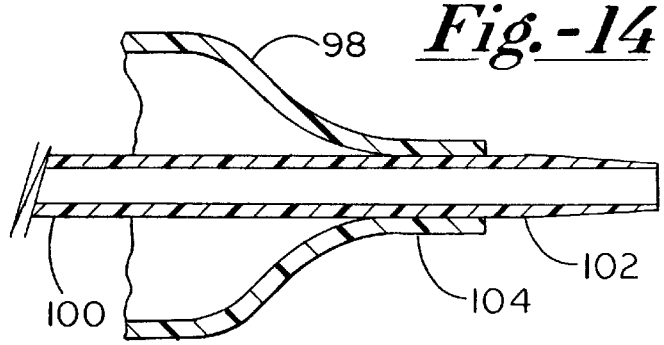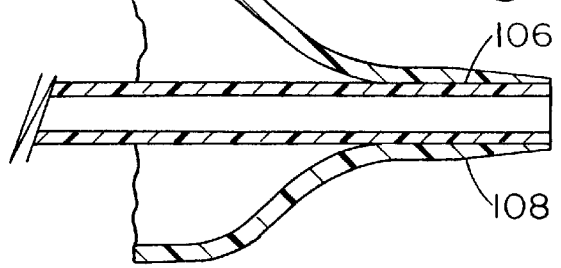

LASER ABLATION OF ANGIOPLASTY CATHETERS AND BALLOONS

This is a Divisional of application Ser. No. 08/582,371, filed on Jan. 11, 1996, now U.S. Pat. No. 5,733,301.

BACKGROUND OF THE INVENTION

The present invention relates to dilatation balloon catheters employed in applications such as percutaneous transluminal angioplasty (PTA) and percutaneous transluminal coronary angioplasty (PTCA) procedures, and more particularly to enhancements to such catheters and their dilatation balloons for improved maneuverability in smaller and more tortuous passages of the vascular system.

Dilatation balloon catheters are well known for their utility in treating the build-up of plaque and other occlusions in blood vessels. Typically a catheter is used to carry a dilatation balloon to a treatment site, where fluid under pressure is supplied to the balloon, to expand the balloon against an obstruction.

The dilatation balloon usually is mounted along the distal end region of the catheter and surrounds the catheter. When the dilatation balloon is expanded, its main body portion or medial section has a diameter substantially larger than that of the catheter. Proximal and distal shafts or stems of the balloon have diameters substantially equal to the diameter of the catheter. Proximal and distal tapered sections, or cones, join the medial region to the proximal and distal shafts, respectively. Each cone diverges in the direction toward the medial region. Fusion bonds between the balloon and catheter form a fluid tight seal to facilitate dilatation of the balloon by introduction of a fluid under pressure.

Along with body tissue compatibility, primary attributes considered in the design and fabrication of dilatation balloons are strength and pliability. A higher hoop strength or burst pressure reduces the risk of accidental rupture of a balloon during dilatation.

Pliability refers to formability into different shapes, rather than elasticity. In particular, when delivered by the catheter, the dilatation balloon is evacuated, flattened and generally wrapped circumferentially about the catheter distal region. Thin, pliable dilatation balloon walls facilitate a tighter wrap that minimizes the combined diameter of the catheter and balloon during delivery. Furthermore, pliable balloon walls enhance the catheter "trackability" in the distal region, i.e. the capability to bend in conforming to the curvature in vascular passages.

One method of forming a strong and pliable dilatation balloon of polyurethane terephthalate (PET) is disclosed in U.S. Pat. No. Re. 33,561 (Levy). A tubing of PET is heated at least to its second order transition temperature, then drawn to at least triple its original length to axially orient the tubing. The axially expanded tubing is then radially expanded within a generally cylindrical form, to a diameter at least triple the original diameter of the tubing. The form defines the aforementioned main body, shafts and cones, and the resulting balloon has a burst pressure of greater than 200 psi.

Such balloons generally have a gradient in wall thickness along the cones. In particular, larger dilatation balloons (e.g. 3.0–4.0 mm diameter when expanded) tend to have a wall thickness along the main body in the range of 0.004–0.0008 inches (0.010–0.020 mm). Near the main body, the cones have approximately the same wall thickness. However, the wall thickness diverges in the direction away from the main body, until the wall thickness near each shaft is in the range of 0.001–0.0025 inches (0.025–0.063 mm). Smaller dilatation balloons (1.5–2.5 mm) exhibit the same divergence in the cone walls, i.e. from 0.0004–0.0008 inches near the main body to 0.0008–0.0015 inches (0.02–0.04 mm) near the associated shaft or stem.

The increased wall thickness near the stems does not contribute to balloon hoop strength, which is determined by the wall thickness along the balloon medial region. Thicker walls near the stems reduce maneuverability of the balloon and catheter. The dilatation balloon cannot be as tightly wrapped, meaning its delivery profile is larger, limiting the capacity of the catheter and balloon for treating occlusions in smaller vessels.

U.S. Pat. No. 4,963,133 (Noddin) discloses an alternative approach to forming a PET dilatation balloon, in which a length of PET tubing is heated locally at opposite ends and subjected to axial drawing, to form two "necked down" portions which eventually become the opposite ends of the completed balloon. The necked down tubing is simultaneously axially drawn and radially expanded with a gas. The degree to which the tubing ends are necked down is said to provide control over the ultimate wall thickness along the tapered walls (or cones), so that the wall thickness can be equal to or less than the wall thickness along the main body. This approach, however, is said to result in a comparatively low burst pressure, only about 8 atmospheres.

Therefore, it is an object of the present invention to provide a dilatation balloon having a high burst pressure and hoop strength, without a gradient of increasing wall thickness along its proximal and distal cones.

Another object is to provide a process for fabricating a dilatation balloon having considerable hoop strength yet more maneuverability for treatment of occlusions in smaller, more tortuous arterial passageways.

A further object is to provide a balloon with portions of the balloon wall selectively thinned to enable a tighter wrapping of the balloon circumferentially about a catheter distal end region, for a reduced profile during balloon delivery.

Yet another object is to provide a process for selectively ablatively removing material from a balloon catheter and its dilatation balloon, to enhance catheter trackability and maneuverability without crystallization, embrittlement or other thermal degradation of material.

SUMMARY OF THE INVENTION

To achieve these and other objects, there is provided a body insertable and expandable device. The device includes a pliable and body compatible dilatation balloon having a mounting region adapted for fluid tight bonding to a catheter or other delivery device. The dilatation balloon has a working region substantially larger in diameter than the mounting region and adapted to engage tissue at a treatment site responsive to expansion of the dilatation balloon. The balloon further has a tapered region between the working region and the mounting region and diverging in the direction from the mounting region toward the working region. The dilatation balloon has a burst pressure of at least about 10 atmospheres and, along the tapered region, has a substantially uniform wall thickness.

Preferably, given a dilatation balloon with a nominal wall thickness throughout the working region, the tapered region wall thickness is no more than twice the nominal wall thickness. Even more preferably, the wall thickness along the tapered region is no more than about 1.5 times the nominal wall thickness.

Typically the mounting region includes proximal and distal mounting sections at opposite ends of the dilatation balloon, and the working region includes a medial working section of the balloon. The tapered region then includes proximal and distal tapered sections disposed between the medial section and the proximal and distal mounting sections, respectively.

If desired, the wall thickness along the tapered sections can be about equal to the nominal wall thickness.

The body insertable and expandable device is fabricated according to a process that includes:

directing an excimer laser beam onto a biaxially oriented balloon at a selected location along an exterior surface of the balloon, to ablatively remove polymeric material and thereby reduce a wall thickness of the balloon at the selected location.

The fabrication of the body insertable and expandable device also can include the following steps as a prelude to the excimer laser direction:

a) axially drawing a length of polymeric tubing to substantially elongate a length of the tubing while heating the tubing to a temperature above its second order transition temperature, to axially orient the tubing;

b) radially expanding the tubing to substantially increase the diameter along at least a portion of the tubing length while maintaining the tubing above the second order transition temperature, to radially orient the tubing, thus to form a biaxially oriented balloon with a medial section having a nominal diameter and a nominal wall thickness, proximal and distal end mounting sections and proximal and distal tapered sections between the medial section and the proximal and distal end mounting sections respectively;

c) allowing the biaxially oriented balloon to cool below the second order transition temperature.

The ablative material removal thins the dilatation balloon wall along the tapered sections, preferably to the point where such wall thickness is approximately the same as the nominal wall thickness along the medial working section. Alternatively the tapered sections may have thicknesses greater than the nominal wall thickness, but with a substantially reduced thickness gradient. In either event, the thinning step increases balloon maneuverability by increasing flexibility near the mounting sections, and allows a tighter wrapping of the balloon for a reduced delivery profile.

The ablation preferably is accomplished with an excimer laser beam, at a wavelength of 193 nm. While other wavelengths (e.g. 248 nm, 308 nm) can yield satisfactory results, the wavelength of 193 nm is best suited for minimizing thermal effects for ablation of a PET dilatation balloon. The fluence level at the surface preferably is in the range of about 100–800 mJ/cm$^2$, and more preferably is about 160 mJ/cm$^2$. The excimer laser beam is pulsed at a repetition rate in the range of about 10–50 pulses per second, with each pulse lasting in the range of about 10–15 ns.

Within the operable limits, the fluence, pulse repetition rate, pulse duration and of course the total number of pulses can be selectively varied to control the nature of excimer laser energy ablation. The polymeric balloon and catheter materials have characteristically high absorptivity, and thus limit the depth of energy penetration and material removal. For example, the PET balloon material can be removed in ultra thin layers on the order of a micron or a fraction of a micron, depending largely upon the selected fluence. Higher levels of fluence remove greater thicknesses of material, but also tend to increase thermal effects. Pulse duration and pulse frequency can be increased to increase the amount of material removal, although again tending toward thermal effects.

In any event, in the context of thinning a catheter balloon wall by about 0.01 mm (for example), single micron or fraction of a micron increments provide precise and controlled removal of material.

Exposure of polymeric materials to excimer laser energy is believed to have photo-chemical and photo-thermal aspects. The former involves the breaking of bonds and disassociation of molecules, leading to momentary pressure increases that eject material, with little or no thermal damage. Photo-thermal effects are the result of molecular vibrational energy. The photo-thermal effects can be minimized by minimizing the energy wavelength (i.e. selecting 193 nm) and by minimizing the fluence. As a result, material is removed essentially without any substantial crystallizing, embrittling or other undesirable altering of the remaining polymeric material. Further as a result of treatment, the wetting characteristics of the polymeric material are changed favorably, so that the surface is more hydrophilic and less thrombogenic.

There are several approaches to removing material from the tapered sections of a dilatation balloon. The balloon can be supported on a mandrel and inflated to give the tapered section a truncated conical profile. Then, with the excimer laser beam oriented perpendicular to the balloon cone angle, ablation proceeds as the mandrel and balloon rotate. Alternatively the balloon may be stationary, with the excimer laser beam "rotated" with mirrors or other optical components.

Yet another alternative involves positioning the evacuated balloon against a plate in a flattened orientation, prior to its bonding to the catheter. Then, the excimer laser beam is traversed across the cones, and if desired, the shafts as well. After ablation of one side, the balloon is turned over and the reverse side ablated.

The catheter also can be ablated at other locations, e.g. at the distal tip that extends beyond the distal cone of the dilatation balloon. Selective ablation can provide a distally converging distal tip, to improve trackability in terms of negotiating sharp turns in vascular passages.

Thus in accordance with the present invention, polymeric material is removed from catheters and dilatation balloons by selective excimer laser ablation to reduce dilatation balloon wrapping profiles and increase flexibility in the balloon and catheter for accommodating curvature in arterial passageways and other body cavities. The improvements are achieved without any reduction in dilatation balloon hoop strength or burst pressure.

IN THE DRAWINGS

For a further appreciation of the above and other advantages, reference is made to the following detailed description and to the drawings, in which:

FIG. 1 is a side elevational view of the distal region of a balloon catheter;

FIGS. 2 and 3 schematically illustrate fabrication of dilatation balloon of the catheter;

FIG. 5 is a schematic view of an apparatus for further fabricating the dilatation balloon;

FIG. 6 is a schematic view similar to the sectional view of FIG. 4, illustrating use of the apparatus to remove material from the dilatation balloon;

FIG. 7 is a sectional view similar to that in FIG. 4, showing the dilatation balloon after excimer laser ablation;

FIGS. 11 and 12 illustrate ablatively formed grooves in a dilatation balloon;

FIG. 13 illustrates use of the apparatus of FIG. 5, after adjusting the laser beam approach angle, for removing material from a distal tip of a catheter;

FIG. 14 shows the catheter distal tip after ablation; and

FIG. 15 shows an alternative catheter distal tip after ablation.

DETAILED DESCRIPTION OF THE PREFERRED EMBODIMENT

Figure 1:
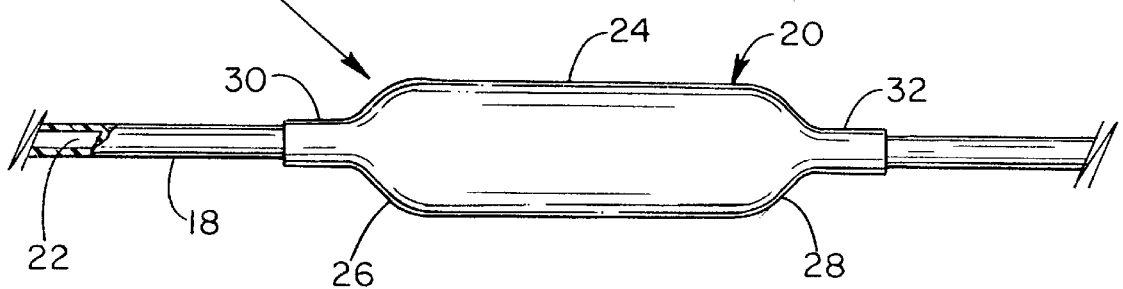

Turning now to the drawings, there is shown in FIG. 1 the distal end region of a balloon catheter 16. The balloon catheter includes an elongate and pliable length of catheter tubing 18 constructed of a body compatible, polymeric material, preferably a polyester such as that sold under the brand name Hytrel. Other suitable materials include polyolefins, polyamides, thermal plastic polyurethanes, and copolymers of these materials. A dilatation balloon 20 surrounds catheter tubing 18 along the distal end region. The dilatation balloon is shown in its fully expanded or dilated configuration, i.e. when the balloon contains a fluid under pressure. The fluid is supplied to the balloon interior through a balloon inflation lumen 22 open to the balloon interior and to the proximal end of catheter tubing 18.

When fully expanded, dilatation balloon 20 includes a main body or medial section 24, essentially an axially extended cylinder substantially concentric about the catheter tubing. Along medial section 24, the dilatation balloon has a diameter much larger than the diameter of catheter tubing 18. For example, the catheter tubing outside diameter can be about 0.04 inches (1 mm). The balloon diameter along medial working section 24 typically is in the range of 3.0–4.0 mm, or in the range of 1.5–2.5 mm for treating obstructions in smaller vascular passageways. At opposite ends of the medial section are a proximal tapered section or cone 26 and a distal tapered section or cone 28. The proximal cone converges in the direction away from the medial section toward an annular proximal mounting section or stem 30. The inner diameter of stem 30 is substantially equal to the outer diameter of the catheter tubing, to provide an annular interface region along which the interior surface of stem 30 and the exterior surface of catheter tubing 18 confront one another and are contiguous.

Similarly, distal cone 28 converges in the distal direction from medial section 24 to a distal mounting section or stem 32. The inner diameter of the distal stem is essentially equal to the catheter outer diameter in the region of stem 32. Frequently the diameter of distal stem 32 is less than the inner diameter of proximal stem 30, because the catheter tubing 18 typically is narrower near the distal stem than it is near the proximal stem.

Dilatation balloon 20 is constructed of a polymeric material, preferably polyethylene terephthalate (PET). Other suitable materials include polyethylene and polyamide. Balloon 20 is sufficiently pliable to enable and facilitate its assumption of a delivery configuration in which the balloon is evacuated and is wrapped circumferentially about the catheter tubing. This reduces the transverse profile of the catheter and balloon, enabling delivery of the dilatation balloon within smaller vascular passageways.

Further, responsive to a fluid under pressure supplied through its interior, balloon 20 must readily assume the expanded configuration shown in FIG. 1. Because the PET or other balloon material is relatively inexpansible as well as pliable, balloon 20 tends to maintain the configuration shown in FIG. 1 under increased fluid pressure within the balloon, up to a burst pressure (much larger than pressures occurring during use) at which rupture occurs.

Figure 2:
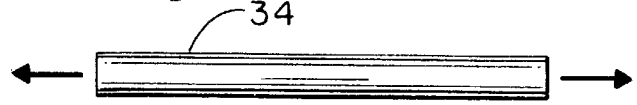
Figure 3:
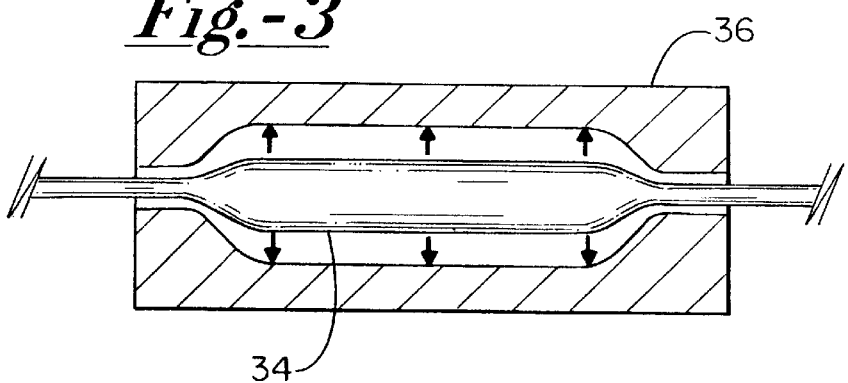

FIGS. 2 and 3 schematically illustrate fabrication of dilatation balloon 20. Initially a length of PET tubing 34 is subjected to an axial tensile force as indicated by the arrows, while being heated to a temperature above the second order transition temperature (e.g. 90° C.). Sufficient force is applied to extend tubing 34 to at least three times its original length, to axially orient the tubing. Then, the axially extended tubing is radially expanded within a form 36 having an internal profile for defining an expanded balloon shape. Expansion is accomplished by closing off one end of the tubing, then supplying a gas (e.g. nitrogen) under pressure to the tubing interior. The PET tubing becomes biaxially oriented as a result of the radial expansion. For further information regarding this approach to dilatation balloon fabrication, reference is made to U.S. Pat. No. Re 33,561 (Levy), said reissue patent being incorporated herein by reference.

Figure 4:
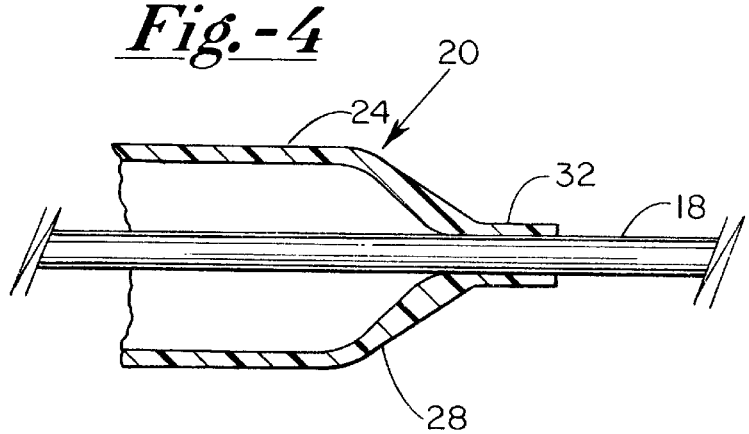
FIG. 4 is an enlarged sectional elevation showing a distal portion of the dilatation balloon.

Dilatation balloon 20, fabricated as described to this point, is shown partially (distal portion) in FIG. 4, it being understood that the proximal portion of the dilatation balloon exhibits similar profile and wall thickness characteristics. Along medial section 24, the dilatation balloon has a wall thickness $t_1$ in the range of 0.0004–0.0008 inches (0.01–0.02 mm). Along tapered section 28 there is a wall thickness gradient. More particularly, the wall thickness is substantially equal to $t_1$ near the medial section, then gradually increases to a thickness in the range of 0.001–0.0025 inches (0.025–0.062 mm) adjacent distal stem 32.

The hoop strength of dilatation balloon 20 is determined by the formula:

$$\sigma = pd/2t;$$

where $\sigma$ is the hoop strength, p is the pressure, d is the dilatation balloon diameter and t is the wall thickness. The maximum diameter d is along medial section 24. Accordingly, hoop strength is determined by wall thickness $t_1$ along the medial section. The excess wall thickness along tapered section 28 contributes nothing to the balloon hoop strength.

Moreover, the excess thickness, particularly near the junction of tapered section 28 and stem 32, is a detriment for several reasons. First, the excess wall thickness increases stiffness at and near the junction. As a result, balloon catheter 16 is less flexible and more difficult to maneuver through curved vascular passageways. Secondly, the increased wall thickness adds to the profile of the balloon. Further, because of the increased stiffness and wall thickness at the junction, balloon 20 is more difficult to flatten and wrap circumferentially about the catheter in the delivery configuration as discussed above. As a result, the profile of the wrapped balloon is larger than necessary, unduly limiting access to smaller vascular passageways.

FIG. 5 illustrates a device 38 for selectively removing polymeric material from balloon catheter 16, reducing its profile and stiffness in the region of the dilatation balloon, and thereby enhancing its maneuverability and utility in smaller, more tortuous body passageways.

Device 38 includes an elongate stainless steel mandrel 40. The outside diameter of the mandrel is approximately equal to the diameter of stems 30 and 32 of the dilatation balloon, to permit a slidable mounting of the balloon onto the mandrel. Mandrel 40 is removably clamped within a jig 42 operable to rotate the mandrel about a longitudinal axis. Mandrel 40 at its opposite end is supported within a guide 44 for more stability in its rotation. An excimer laser 46 (ArF) is supported near mandrel 40 and generates an excimer laser beam 48 shaped by an optical assembly 50 including a converging lens for focusing beam 48 onto the exterior surface 52 of the dilatation balloon along tapered section 28. A mask 54 is interposed between the laser and balloon surface 52 to more sharply define the area selected for treatment. Mandrel 40 incorporates a lumen (not shown) for expanding dilatation balloon 20, so that the balloon when mounted on the mandrel assumes its expanded shape, with tapered sections 26 and 28 having truncated conical configurations. Excimer laser beam 48 preferably is perpendicular to the dilatation balloon exterior surface along tapered section 28.

The dilatation balloon rotates with mandrel 40. The laser, beam conditioning optics and mask are movable generally axially and radially, but more particularly parallel to the profile of tapered section 28 as indicated by the arrows in the figure. Thus beam 48 can be caused to impinge upon any selected portion of the balloon's exterior surface along the tapered section.

In practice, dilatation balloon 20 can be rotated in stepped fashion, timed in accordance with the pulses of excimer laser beam 48. As illustrated in FIG. 6, polymeric material can be removed progressively, proceeding from a portion of the tapered section surface near the medial section 24 toward stem 32. In the figure, a portion of the PET has been removed from tapered section 28 by laser ablation. A broken line at 56 indicates the original tapered section profile. Material to be removed is indicated at 58, with the other material showing the desired profile of tapered section 22 following treatment, i.e. showing a substantially uniform wall thickness equal to thickness $t_1$ along the medial section. While this degree of material removal is preferred, it can be understood that any amount of material removal that substantially reduces the wall thickness gradient is beneficial.

Excimer laser ablation of the polymeric material forms a channel in the polymeric material, approximately equal in depth to the diameter of beam 48, which preferably is focused or nearly focused at the exterior surface. Rotation of balloon 20 and translation of the laser assembly can be continuous or stepped. In either event, they occur in concert to ensure complete coverage of the area of intended material removal. This area can be covered in a continuous sweep, i.e. in a close or tight helical pattern, alternatively, the area can be covered in a series of adjacent rings.

It is apparent from FIG. 6 that to achieve a final uniform thickness or to substantially reduce the thickness gradient, material must be removed to a depth that increases progressively in the direction toward stem 32. Preferably, the increased removal is achieved by increasing the number of incremental episodes (i.e. individual pulses) applied to the surface near the stem, rather than by increasing the pulse duration or pulse energy (i.e. fluence), which may introduce unwanted thermal effects. Within limits, material removal during a given annular traverse or a single rotation of the balloon can be increased by increasing pulse frequency. However, because of thermal effects from frequencies above about 50 Hz, increasing the number of annular traverses of the balloon is the most effective manner of removing additional material without introducing thermal effects.

Excimer laser ablation, sometimes also called ablative photo decomposition, is believed to have photo-chemical and photo-thermal aspects. The photo-chemical aspect involves breaking chemical bonds to cause disassociation of molecules of the polymeric material subject to excimer laser energy. A highly localized and abrupt increase in pressure results, tending to eject material from the exposed area. The ejected material is heated, but rapidly removes heat from the treatment site by its ejection. Accordingly, any temperature increase at the treatment site is extremely brief, and little or no thermal effect results. At higher fluence levels, longer pulse durations and higher pulse frequencies, photo-thermal effects, which involve vibration of the polymeric molecules, become more apparent. While actual operating parameters can vary with the polymeric material and nature of material removal, the minimizing of thermal effects is important. Excessive concentrations of heat can cause crystallization or localized melting where the polymeric material may become brittle. In either event, catheter flexibility and maneuverability are adversely effected.

Conversely, by selecting a short wavelength (preferably 193 nm), shorter pulse durations, lower pulse frequencies and lower fluence levels, decomposition is primarily photo-chemical and thinning of the catheter balloon walls does not materially reduce balloon and catheter flexibility.

Several factors control the rate of polymeric material removal, within limits that permit removal without unwanted thermal effects. For example, in connection with PET a suitable range for fluence level is 100–800 mJ/cm$^2$. A more preferred range is about 160–750 mJ/cm$^2$, with a preference toward the lower end of this range to minimize thermal effects.

A suitable pulse duration is 10–15 ns with a pulse frequency of about 10–50 pulses/second, and more preferably 10–40 pulses/second. Again, minimizing thermal effects favors the lower portion of the range.

The preferred wavelength as noted is 193 nm (ArF laser), but absorption characteristics of a specific polymer may favor another wavelength, e.g. 248 nm (KrF laser) or 308 nm (XeCl laser), for a peferred range of about 190–310 nm.

To further ensure a complete removal of ablated material, and to further ensure against thermal effects, a stream or flow of gas (e.g. nitrogen) can be directed across the dilatation balloon, particularly at and around the ablation site. The desired flow can be generated with a source of nitrogen under pressure, as indicated at 60. As it exits source 60, the nitrogen undergoes a rapid decrease in pressure and cools, whereupon it tends to cool the ablation area, primarily by convection but also in carrying away heated ablated material.

FIG. 7 illustrates the portion of dilatation balloon 20 shown in FIG. 6 after excimer laser ablation, with all unwanted material removed. The thickness $t_2$ of a dilatation balloon wall 62 along tapered section 28 is substantially uniform, preferably varying by no more than about 10% or at most about 25%, and substantially equal to (e.g. within about within about 25% of, and more preferably 10% of) the thickness $t_1$ of the wall along medial section 24.

While only the distal portion of balloon 20 has been illustrated in detail, a substantially similar laser ablation is performed along proximal tapered section 26. The balloon wall thickness along both tapered sections is substantially reduced, especially near the stems. As a result, balloon 20 is much flatter when evacuated and can be wrapped more tightly about catheter tubing 18 to present a smaller delivery profile. Balloon maneuverability and flexibility are enhanced, due to the substantially reduced stiffness along the tapered sections. These improvements are achieved virtually without crystallization, embrittlement or other undesirable change in morphology. In fact, in PET and many other polymeric materials, a favorable result of excimer laser treatment is a change in wetting characteristics whereby the balloon is more hydrophilic in the treated area. This reduces any tendency to cause or promote clotting.

Figure 8:
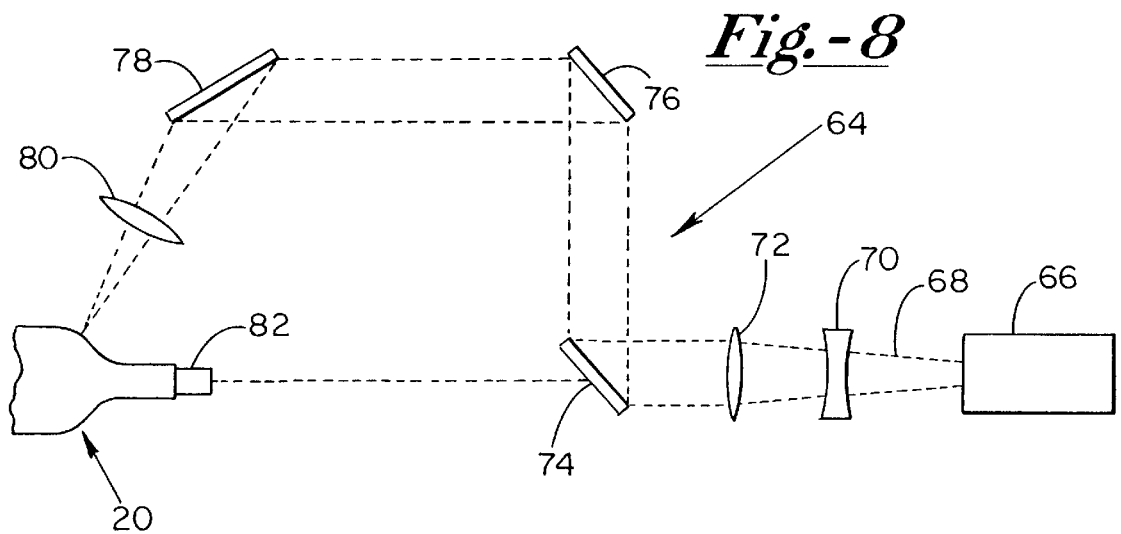
FIG. 8 is a schematic view of an alternative laser ablation apparatus.

FIG. 8 illustrates and alternative apparatus 64 for excimer laser ablation of balloon 20. A stationary excimer laser source 66 generates a beam 68 of the preferred wavelength of 193 nm. Beam 68 is directed through a diverging lens 70 and then through a collimating lens 72. The collimated beam is diverted by a series of planar reflectors 74, 76 and 78, and then through a focusing lens 80 which locates the beam focal point near exterior surface 52 of the dilatation balloon.

Dilatation balloon 20 is supported on an elongate stationary shaft 82 and remains stationary. The required relative movement is achieved by rotating beam 68, in particular by rotating planar reflectors 74–78 about an axis coincident with shaft 82. A sub-assembly including reflector 78 and lens 80 further is pivotable to radially and axially displace the beam along tapered section 28.

Figure 9:
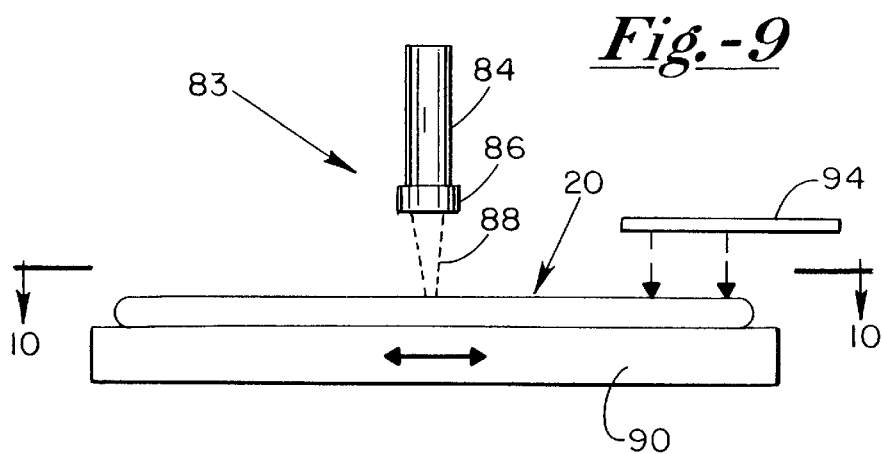
FIGS. 9 and 10 are schematic views of another alternative laser ablation apparatus.
Figure 10:
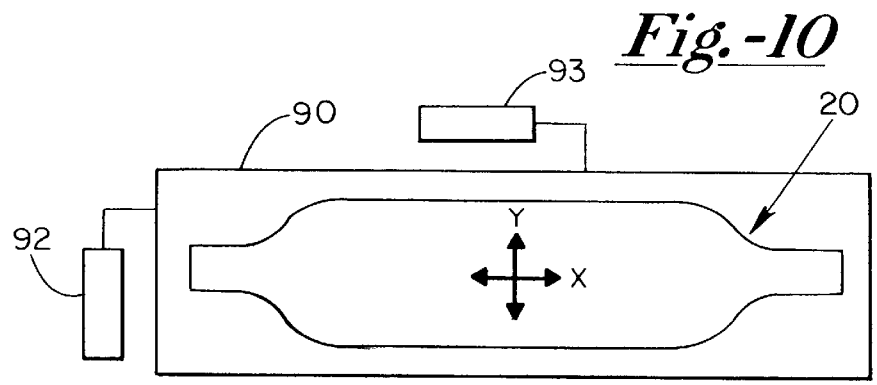

FIGS. 9 and 10 illustrate a further alternative excimer laser ablation apparatus 83 including a laser source 84, an optical assembly 86 for shaping and focusing a laser beam 88 and a movable plate 90 for supporting dilatation balloon 20 in an evacuated, flat configuration. Stepper motors 92 and 93 are provided for translating plate 90 in two perpendicular directions x and y (FIG. 10) that are horizontal, i.e. parallel to the major plane of the flattened balloon. The combined motion of plate 90 creates the effect of a series of adjacent sweeps of beam 88 transversely across tapered sections 26 and 28. To substantially reduce or remove the thickness gradient, the number of sweeps is increased in the direction approaching the stems. When all excess material has been removed from the exposed upper side, dilatation balloon 20 is turned over for removal of material from the opposite side to complete the process. A source of pressurized nitrogen for cooling can be used if desired, as indicated at 94. As an alternative, the desired relative motion can be achieved by translating the laser source and optics, thus to move the beam rather than the dilatation balloon. The primary advantage in using apparatus 83 is that dilatation balloon 20 need not be expanded for removal of material.

While excimer ablation preferably reduces the wall along the tapered sections to a uniform thickness, such need not be the case to substantially improve balloon catheter performance. As seen in FIGS. 11 and 12, material can be selectively ablated to form an array of channels or grooves 96 in a balloon wall 97 along each of the tapered sections. The channels can be uniform in width as shown, or may diverge in the direction toward medial section 24. In either event, the depth of each channel 96 increases in the direction toward the stem. Channels 96 reduce the balloon profile and rigidity along the tapered sections, especially near the stems, and thus reduce the balloon profile, allow a tighter wrapping of the balloon for delivery and enhance catheter maneuverability.

FIG. 13 illustrates device 38 with a dilatation balloon 98 and a catheter 100 supported on rotatable mandrel 40. Excimer laser beam 48 is directed onto a distal tip region 102 of the catheter, which extends beyond a stem 104 of the dilatation balloon. The beam is not perpendicular, but rather is directed onto the tip region at an acute angle with respect to the mandrel rotational axis. Also, beam 48 is not as sharply in focus at the exterior surface. The result is a gradient in fluence along the surface of tip region 102 with the fluence level increasing in the distal direction. The result is a tendency in the excimer laser pulses to remove polymeric material to depths that increase in the distal direction. The result is a converging distal tip region, as shown in FIG. 14.

Apparatus 64 can be adjusted to achieve the same result, if it is desired to maintain the balloon stationary during ablation. As seen in FIG. 15, the technique can be used to remove dilatation balloon material in a catheter in which the catheter tubing 106 does not extend distally beyond a balloon stem 108. In both cases there is a reduction in tip profile and less stiffness at the distal tip, tending to enhance catheter maneuverability.

Thus in accordance with the present invention, controlled excimer laser ablation selectively thins the walls of dilatation balloons and catheters. The invention enables fabrication of dilatation balloons according to a process that yields favorably high burst pressures, while eliminating or substantially reducing an undesirable gradient in wall thickness. The result is a dilatation balloon with the desired burst pressure but without the excess wall thickness, particularly along the tapered sections near the balloon stems. Co-extruded or multi-layered balloons, although not shown, can be fabricaed or treated according to this technique. While the preceding description features dilatation balloons and catheters, it is to be appreciated that the invention can apply to other balloons and catheters as well, e.g. catheters with balloons expandable to deploy prostheses, more particularly to enlarge plastically deformable stents. Catheter balloons intended for use in body passages other than vascular passages, likewise are enhanced when fabricated or treated according to the invention. With appropriately thinned walls, the balloon and catheter facilitate tighter balloon wrapping for a reduced delivery profile, and exhibit greater flexibility for maneuvering in small and tortuous vascular passageways.

What is claimed is:

1. A process for fabricating a body insertable and expandable treatment device, including:

directing an excimer laser beam (48,68,88) onto a biaxially oriented balloon (20,98) at a selected location along an exterior surface of the balloon, to ablatively remove polymeric material and thereby effect a thinning of a balloon wall of the dilatation balloon at the selected location.

2. The process of claim 1 further including the following steps, performed prior to said directing of the excimer laser beam:

axially drawing a length of polymeric tubing (34) to substantially increase a length of the tubing while heating the tubing to a temperature above its second order transition temperature, to axially orient the tubing;

radially expanding the tubing to substantially increase its diameter along at least a portion of the tubing length, while maintaining the tubing above said second order transition temperature, to radially orient the tubing, thus to form a biaxially oriented balloon with a medial section (24) having a nominal diameter and a nominal wall thickness, proximal and distal end mounting sections (30,32), and proximal and distal tapered sections (26,28) between the medial section and the proximal and distal end mounting sections respectively;

allowing the biaxially oriented balloon to cool below the second order transition temperature.

3. The process of claim 2 wherein:

each of the tapered sections has a gradient of increasing wall thickness in the direction from the medial section toward the associated end mounting section, said selected location comprises the tapered sections, and said thinning of the balloon wall reduces the gradient.

4. The process of claim 3 wherein:

said thinning substantially eliminates the gradient.

5. The process of claim 2 wherein:

the selected location includes portions of the tapered sections, and the removal of the polymeric material forms an array of channels (96) in each of the tapered sections.

6. The process of claim 1 wherein:

said excimer laser beam has a wavelength of about 193 nm.

7. The process of claim 1 wherein:

said step of directing an excimer laser beam is performed with a fluence level, at the surface of the balloon, in the range of about 100–800 mJ/cm$^2$.

8. The process of claim 1 wherein:

the directing of the excimer laser beam includes pulsing the beam at a repetition rate in the range of about 10–50 pulses per second.

9. The process of claim 8 wherein:

the repetition rate is about 10 pulses per second.

10. The process of claim 8 wherein:

said pulses have a duration in the range of about 10–15 ns.

11. The process of claim 1 further including:

convectively cooling the biaxially oriented balloon during said directing of the excimer laser beam onto the surface of the balloon.

12. The process of claim 1 wherein:

said directing of an excimer laser beam includes orienting the beam substantially perpendicular to the surface at the selected location.

13. The process of claim 1 wherein:

said directing of the excimer laser beam includes orienting the beam at an acute angle with respect to the surface at the selected location, to provide a gradient in fluence across the surface at the selected location.

14. A process for selectively shaping a body insertable device including a polymeric balloon dilatation catheter (18,100,106) and a dilatation balloon (20,98) bonded in fluid tight fashion to a distal end region of the catheter, the dilatation balloon having a medial section (24) with a nominal wall thickness and a nominal diameter when the balloon is expanded, proximal and distal end mounting sections (30,32) bonded to the catheter, and proximal and distal tapered sections (26,28) between the medial section and the proximal and distal end mounting sections, respectively, each of the tapered sections having a gradient of increasing wall thickness in the direction from the medial section toward the associated end mounting section: said process for selectively shaping the device including:

directing an excimer laser beam (48,68,88) onto the device to irradiate an exterior surface of the device at a fluence within the range of about 100–800 mJ/cm$^2$, to ablatively remove polymeric material from the device at selected locations including the tapered sections at least proximate the end mounting sections.

15. The process of claim 14 wherein:

the polymeric material is ablatively removed in a manner to reduce the gradient in wall thickness along the tapered sections.

16. The process of claim 14 wherein:

each of the tapered sections has a substantially uniform wall thickness following said removal of polymeric material.

17. The process of claim 14 wherein:

said removal of polymeric material forms a plurality of grooves in each of the tapered sections.

18. The process of claim 14 wherein:

said directing of the excimer laser beam includes pulsing the laser beam at a frequency in the range of about 10–50 pulses per second.

19. The process of claim 14 wherein:

said excimer laser beam is generated at a wavelength within the range of about 190–310 nm.

20. The process of claim 14 wherein:

said excimer laser beam is pulsed, each pulse having a duration in the range of about 10 to about 15 ns.

21. The process of claim 14 further including:

interposing a mask (54) between a source (46,66,84) of the excimer laser beam and the selected locations when so directing the excimer laser beam, to determine an area of beam impingement onto the exterior surface at the selected locations.

22. The process of claim 14 wherein:

said directing of the excimer laser beam includes supporting the dilatation balloon in an expanded state on a longitudinally extended mandrel (40,82), translating the dilatation balloon and excimer laser beam rotationally relative to one another about an axis that substantially coincides with the mandrel, and linearly translating the dilatation balloon and beam relative to one another longitudinally and radially with respect to said axis.

23. The process of claim 14 wherein:

the directing of the excimer laser beam includes evacuating the dilatation balloon and maintaining the balloon in a substantially flat state, orienting the excimer laser beam substantially perpendicular to a major plane of the dilatation balloon when in the substantially flat state, and translating the beam and dilatation balloon with respect to one another in mutually perpendicular directions parallel to the major plane.

* * * * *